April 16, 1940. B. E. PRIOR Plant Pat. 377
ROSE PLANT
Filed June 9, 1939
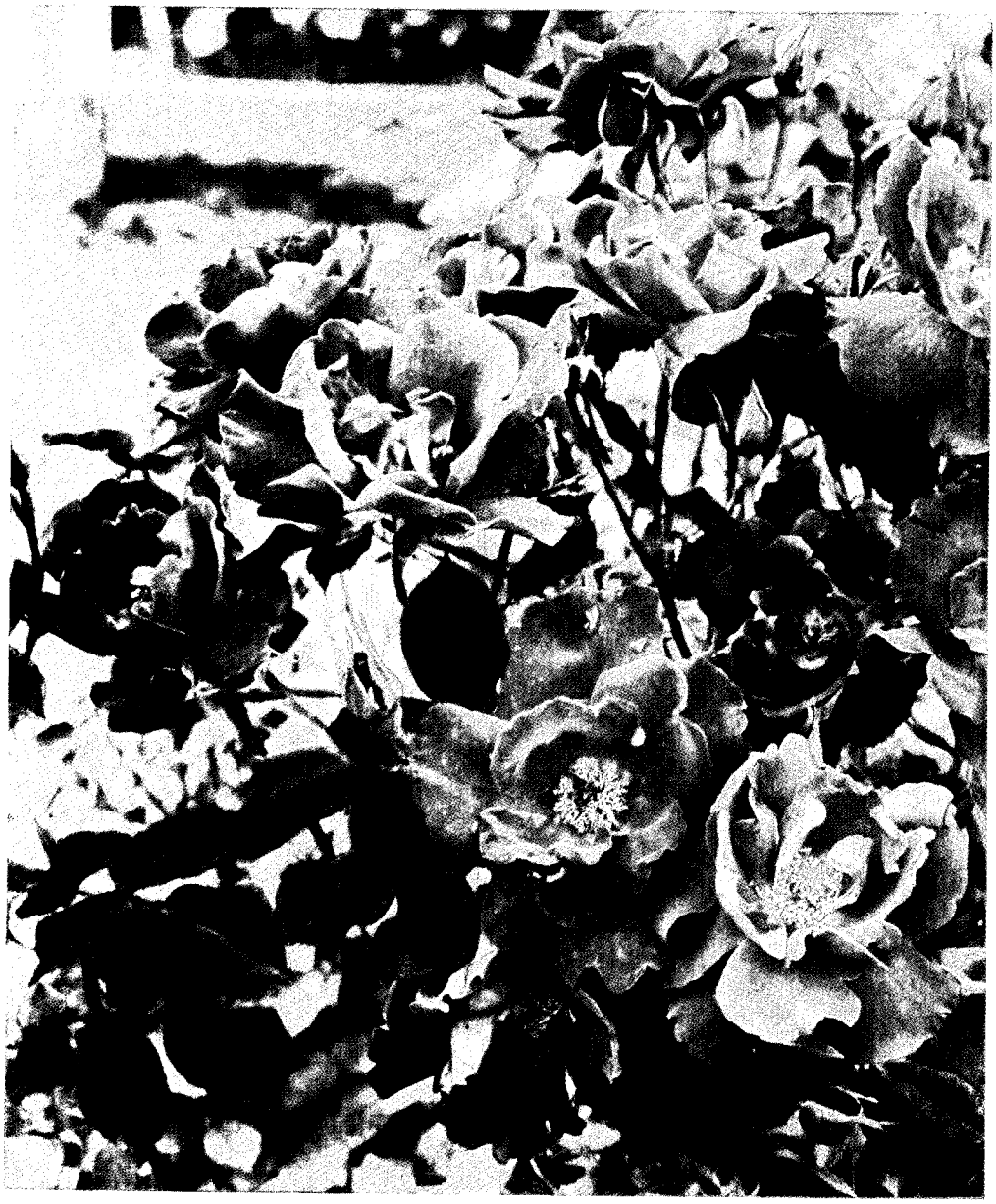
Inventor
B. E. Prior
By Robb & Robb
attorneys Patented Apr. 16, 1940

UNITED STATES PATENT OFFICE

377

ROSE PLANT

Basil Edmund Prior, Colchester, England, assignor to Jackson & Perkins Company, Newark, N. Y.

Application June 9, 1939, Serial No. 278,346

1 Claim. (Cl. 47—61)

This invention relates to a new and distinct Hybrid Polyantha Rose, the result of a cross between an unnamed seedling and the well-known polyantha D. T. Poulsen having as its objective the development of a floribunda rose distinguished by color, form and habit for mass effect.

This new variety proves itself to be superior in type owing to its (1) vigorous bush, covering three feet in circumference with a growth of two to three feet in height within a year; (2) its striking red masses of color which are prominently visible from great distances in pleasing effect; (3) its continuity of bloom and interesting habit of always having some individual flowers in addition to the large clusters and masses contrasting with its luxuriant green foliage.

The foregoing characteristics have been found to be fixed in asexual reproduction of the variety.

The following is a detailed description of this new rose, the color terminology employed therein being in accord with Ridgway's Color Standard.

Parentage:

*Seed parent.*—Unnamed.

*Pollen parent.*—D. T. Poulsen.

Classification:

*Botanic.*—Polyantha and large flowered Polyantha.

*Commercial.*—Floribunda.

*Flower*

Blooming habit:

Observations made at Newark, New York, in September, 1938.

*Recurrent.*—Continuous.

Always color on the bush, sometimes more than others.

Bud:

*Size.*—Small.

*Form.*—Ovoid, unaffected by wet or hot weather.

*Color.*—When sepals first divide—Carmine, Plate 1. When petals begin to unfurl—Carmine, Plate 1. When half blown: inside of petals—Spectrum Red, Plate 1; reverse of petals—Carmine, Plate 1.

*Sepals.*—Branched. Curl back when half open.

*Calyx.*—Shape—funnel. Size—small. Aspect—smooth.

*Peduncle.*—Medium length. Aspect—smooth. Color—Light Cress Green, Plate 31. Strength—erect, slender.

*Opening.*—Opens well. Is not affected by adverse conditions.

Bloom:

*Size.*—Medium. Average size when fully expanded 3½".

*Borne.*—In clusters flat.

*Stems.*—Long, strong.

*Form.*—When first open, cupped; retains its form to the end.

*Petalage.*—Semi-single (two rows of petals). Number of petals under normal conditions—15.

*Color.*—Center of flower—between Spectrum Red and Carmine, Plate 1. Outer petals—between Spectrum Red and Carmine, Plate 1. Base of petals (aiglet)—Cadmium Yellow, Plate 3. Inside of petals—between Spectrum Red and Carmine, Plate 1. Reverse of petals—Carmine, Plate 1. General tonality from a distance—Carmine.

*Variegations.*—None.

*Discoloration.*—General tonality at end of first day, Spectrum Red to Carmine. Second day—Spectrum Red to Carmine. Third day—Carmine.

Petals:

*Texture.*—Leathery. Unaffected by wet or hot weather.

*Appearance.*—Inside—shiny. Outside—shiny.

*Form.*—notched.

*Arrangement.*—Irregular. Petaloids in center—few, small.

*Persistence.*—Drop off cleanly.

*Fragrance.*—Slight. Nature—"Old Rose Perfume" (Centifolia).

*Lasting quality.*—On the plant and as cut flower—very long.

Genital organs:

*Stamens, anthers.*—Small, many. Color—Light Cadmium, Plate 4. Arrangement—regular round styles.

*Stamens, filaments (threads).*—Long. Color—Picric Yellow, Plate 4.

*Pollen.*—Pinard Yellow, Plate 4.

*Styles.*—Bunched, uneven length, medium length, thin.

*Stigmas.*—Picric Yellow, Plate 4.
*Ovaries.*—All enclosed in calyx.
Fruit: Variety is fertile.
*Form.*—Depressed top.
*Aspect.*—Smooth.
*Sepals.*—Permanent; recurved.

*Plant*

Form: Bush.
Growth: Vigorous.
Foliage: Five to seven leaflets.
*Size.*—Medium.
*Quantity.*—Normal.
*Color:* New foliage: upper side, edges—Hay's Maroon, Plate 13. Center—Elm Green, Plate 17. Under side, edges—Vandyke Red, Plate 13. Center—Light Cress Green, Plate 31. Old foliage: upper side—Dark Cress Green, Plate 31. Under side—Rainette Green, Plate 31.
*Shape.*—Oval.
*Texture.*—Upper side—leathery, glossy. Under side—rough. Ribs and veins—ordinary.
*Edge.*—Serrated (saw toothed).
*Serration.*—Single.
*Rachis.*—Color—Rainette Green, Plate 31. Under side—prickles.
*Stipules.*—Medium, bearded.
*Disease resistance.*—Resistant.
Wood:
*New wood.*—Color—Light Cress Green, Plate 31. Bark—smooth.
*Old wood.*—Color—Cress Green, Plate 31. Bark—smooth.
Thorns (divided into thorns, prickles, and short needles):
*Thorns:* Quantity: on main stalks from base—few; on laterals from stalk—none. Form—narrow base, short, hooked downward. Color when young—Vandyke Red, Plate 13. Position—irregular.
*Prickles:* Quantity: on main stalks—few; on laterals—few. Color—Chestnut Brown, Plate 14.

Summarizing, this new rose is distinguished by the large Floribunda semi-single flowers, differing in size and shape from any other rose of that type now in commerce; by the deep Carmine color and extra rows of petals, the semi-cup shape of the flowers; by the brilliant single flowers which appear in the intervals between the very heavy masses of clusters, and the well balanced dark green, unusually disease resistant and abundant foliage.

I claim:

A new and distinct Floribunda Rose plant characterized as to novelty by its vigorous and fast growth, its vivid color display of clean and flat red masses of blooms and continuity of bloom of large clusters with some individual flowers strongly contrasting with the luxuriant dark green foliage, substantially as shown and described.

BASIL EDMUND PRIOR.